United States Patent
Helm et al.

(10) Patent No.: US 9,317,661 B2
(45) Date of Patent: Apr. 19, 2016

(54) AUTOMATIC IMPLANT DETECTION FROM IMAGE ARTIFACTS

(71) Applicant: Medtronic Navigation, Inc., Louisville, CO (US)

(72) Inventors: Patrick A. Helm, Milton, MA (US); Shuanghe Shi, Southborough, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 14/543,385

(22) Filed: Nov. 17, 2014

(65) Prior Publication Data

US 2015/0078647 A1    Mar. 19, 2015

Related U.S. Application Data (63) Continuation of application No. 13/355,929, filed on Jan. 23, 2012, now Pat. No. 8,891,847.

(51) Int. Cl.
  *G06K 9/00*   (2006.01)
  *G06F 19/00*  (2011.01)
  *G06T 11/00*  (2006.01)
  (Continued)

(52) U.S. Cl.
  CPC ............ *G06F 19/3437* (2013.01); *A61B 6/032* (2013.01); *A61B 6/12* (2013.01); *A61B 6/5258* (2013.01); *G06K 9/64* (2013.01); *G06T 7/0014* (2013.01); *G06T 11/00* (2013.01); *G06T 11/008* (2013.01); *G06T 19/20* (2013.01); *A61B 6/4405* (2013.01); *G06T 2207/10028* (2013.01); *G06T 2207/10124* (2013.01); *G06T 2207/20092* (2013.01); *G06T 2207/20221* (2013.01); *G06T 2207/30004* (2013.01); *G06T 2207/30052* (2013.01); *G06T 2219/2004* (2013.01)

(58) Field of Classification Search
  CPC ........ A61B 6/032; A61B 6/12; A61B 6/5258; A61B 6/4405; G06F 19/3437; G06K 9/64; G06T 11/00; G06T 11/008; G06T 19/20; G06T 7/0014; G06T 2207/10028; G06T 2207/10124; G06T 2207/20092; G06T 2207/20221; G06T 2207/30004
  See application file for complete search history.

(56) References Cited

U.S. PATENT DOCUMENTS 5,933,471 A  8/1999  Kalvin
6,510,198 B2 1/2003  Simon et al.
(Continued)

OTHER PUBLICATIONS

Stayman et al (likelihood-based CT reconstruction of objects containing known components, 11th international meeting on fully 3D image reconstruction in radiology and nuclear medicine, Jul. 15, 2011).*

(Continued)

*Primary Examiner* — Amara Abdi
(74) *Attorney, Agent, or Firm* — Harness, Dickey (57) ABSTRACT

A computer-implemented method of implant detection includes receiving a three-dimensional (3D) image of an anatomy portion of a patient from computed tomography (CT) projections of the patient in an image processing computing system. A cluster of voxels forming an implant candidate is identified on a CT slice of the 3D image and the identified implant candidate is compared with artifacts of implants from an implant database stored in a memory of the computing system. A best-fit implant is selected from the implant database and a graphical image of the best-fit implant is overlaid on the CT slice on a display of the computing system.

26 Claims, 7 Drawing Sheets

(51) Int. Cl.
  G06T 7/00 (2006.01)
  A61B 6/03 (2006.01)
  A61B 6/12 (2006.01)
  G06K 9/64 (2006.01)
  G06T 19/20 (2011.01)
  *A61B 6/00* (2006.01)

(56) References Cited

U.S. PATENT DOCUMENTS

| | | | |
|---|---|---|---|
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,369,695 B2 | 5/2008 | Zettel et al. | |
| 8,238,631 B2 | 8/2012 | Hartmann et al. | |
| 8,311,791 B1* | 11/2012 | Avisar | G09B 23/28 702/19 |
| 8,891,847 B2 | 11/2014 | Helm et al. | |
| 2009/0074278 A1 | 3/2009 | Beaulieu et al. | |
| 2010/0049195 A1* | 2/2010 | Park | A61B 5/055 606/87 |
| 2010/0183214 A1 | 7/2010 | McCollough et al. | |
| 2010/0290690 A1 | 11/2010 | Hartmann et al. | |
| 2011/0081071 A1 | 4/2011 | Benson et al. | |
| 2012/0008845 A1* | 1/2012 | Ning | A61B 6/032 382/131 |
| 2012/0038173 A1* | 2/2012 | Carlos | F02C 6/00 290/1 R |
| 2013/0006094 A1* | 1/2013 | Charles | A61B 5/055 600/411 |
| 2013/0188848 A1 | 7/2013 | Helm et al. | |
| 2013/0243298 A1* | 9/2013 | Bredno | G06T 5/50 382/131 |

OTHER PUBLICATIONS

Yamazaki et al ("Improvement of the Depth position in 2D/3D registration of Knee implants using single-plane Fluoroscopy", IEEE Transaction on Medical imaging, vol. 23, No. 5, May 2004).*

"A pragmatic approach to metal articact reduction in CT: merging of metal artifact reduced images," Watzke et al., pp. 849-856 (copyright 2004 Springer-Verlag).

"Artifacts in CT: Recognition and Avoidance," Barrett et al., RadioGraphics 2004; 14:1679-1691, pp. 1679-1691; (copyright 2004, RSNA).

"General three-dimensional image simulation and surface reconstruction in scanning probe microscopy using a dexel representation," Qian et al., ScienceDirect, 0304-3991, p. 29-42 (copyright 2007 Elsevier B.V.).

"Interactive Segmentation and Three-Dimension Reconstruction for Cone-Beam Computed-Tomography Images," Suebnukarn et al., 8 pages, 2008.

"Normalized Metal Artifact Reduction (NMAR) in Computed Tomography," Meyer et al., Medical Physics, 2010, vol. 37, 5 pages.

"Reducing Metal Artifacts in Cone-Beam CT Images by Preprocessing Projection Data," Zhang, et al., Int. J. Radiation Oncology Biol. Phys., vol. 67, No. 3, pp. 924-932 (Copyright 2007 Elsevier Inc.).

"Suppression of Metal Artifacts in CT Using a Reconstruction Procedure That Combines MAP and Projection Completion," Lemmens, et al., IEEE Transactions on Medical Imaging, vol. 28, No. 2, Feb. 2009, pp. 250-260.

International Preliminary Report on Patentability and Written Opinion mailed Aug. 7, 2014 for PCT/US2013/022508 claiming benefit of U.S. Appl. No. 13/355,929, filed Jan. 23, 2012.

International Search Report and Written Opinion mailed May 14, 2013 for PCT/US2013/022508 claiming benefit of U.S. Appl. No. 13/355,929, filed Jan. 23, 2012.

Stayman et al (likelihood-based CT reconstruction of objects containing known components, 11th international meeting on fully 3D image reonstruction in radiology and nuclear medicine, Jul. 15, 2011).

Yamazaki et al ("Improvement of the Depth position in 2D/3D registration of Knee implants using single-plane Fluoroscopy", IEEE Transaction on Medical Imaging, vol. 23, No. 5, May 2004.

* cited by examiner

AUTOMATIC IMPLANT DETECTION FROM IMAGE ARTIFACTS

CROSS-REFERENCE TO RELATED APPLICATIONS

This application is a continuation of U.S. patent application Ser. No. 13/355,929 filed on Jan. 23, 2012, the entire disclosure of which is incorporated herein by reference.

FIELD

The present disclosure relates to detection and correction of artifacts caused by implants x-ray related imaging.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

The present teachings provide a computer-implemented method of implant detection includes receiving a three-dimensional (3D) image of an anatomy portion of a patient from computed tomography (CT) projections of the patient in an image processing computing system. A cluster of voxels forming an implant candidate is identified on a CT slice of the 3D image and the identified implant candidate is compared with artifacts of implants from an implant database stored in a memory of the computing system. A best-fit implant is selected from the implant database and a graphical image of the best-fit implant is overlaid on the CT slice on a display of the computing system.

In another embodiment, the method includes constructing a three-dimensional (3D) image of an anatomy portion of a patient from computed tomography (CT) projections of the patient in an image processing computing system, displaying the 3D image on a display of the computing system and identifying a cluster of voxels forming an implant candidate on a CT slice of the 3D image. The method includes prompting for user input if an implant candidate is not automatically identified, selecting one of an automatically identified implant candidate and a user identified implant candidate and comparing the implant candidate with artifacts of implants from an implant database stored in a memory of the computing system. A best-fit implant is selected from the implant database and a graphical image of the best-fit implant is overlaid on the CT slice on a display of the computing system. The graphical image of the best-fit implant is edited by user input.

The present teachings also provide an image processing system for detecting an implant. The system includes a computer processor including memory storage and an image processing software module, an implant database accessible by the processor, a display and an input device. The processor is configured to construct a three-dimensional (3D) image of an anatomy portion of a patient from computed tomography (CT) projections of the patient in an image processing computing system, to display the 3D image on the display and to detect an implant candidate in a CT slice of the 3D image. The processor is also configured to identify the implant candidate from the implant database and select the best-fit implant, and to overlay a graphical image of the best-fit implant on the CT slice.

The present teachings further provide selecting the best-fit implant using a least square, weighted, iterative or other optimization method. Reliability analysis can also be applied. The overlaid implant is colorized with a selected transparency and contrast with optional user input through an input device of the computing system.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

The following description is merely exemplary in nature. It should be understood that throughout the drawings, corresponding reference numerals indicate like or corresponding parts and features. As indicated above, the present teachings are directed toward an imaging system, such as an O-Arm® imaging system commercially available from Medtronic Navigation, Inc., Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

The present teachings are directed to a method of correcting artifacts caused by hardware, such as screws or other implants, in portions of the anatomy of a subject undergoing imaging by scanning methods using x-ray sources. Such implants tend to obscure the underlying anatomy of reconstructed three-dimensional (3D) images and make critical assessment of a condition (such as a defect or other pathology) or delivered therapy, including evaluating the positioning of implants, difficult.

Artifacts from implants pose a problem, for example, in x-ray computed tomography (CT), including cone beam CT (CBCT) and in other imaging methods using an x-ray source. Artifacts from implants arise because the attenuation coefficient of materials used for implants, such as, for example, metals, metal alloys, ceramics, etc., is higher than the attenuation coefficient of bones and soft tissue in the range of x-ray intensities used in such CT imaging. Flat panel detectors used to capture the images can also cause scatter that leads to artifacts at implant locations. Various methods of metal artifact reduction rely on computationally complex algorithms to remove the artifacts, use interpolation methods to fill the gaps, and re-projection of the images during 3D image reconstruction. Such methods are often difficult to implement in the operating/diagnostic imaging environment.

The present teachings provide a method for identifying an implant associated with an artifact in one or more CT slices (axial planar sections of the 3D image) after the 3D image reconstruction from a comparison database using a best fit and/or reliability method. After the best fit implant is selected from the database, an image of the selected implant is overlaid on the corresponding artifact. This correction is done after processing of the CT images for 3D reconstruction. The correction is performed on the reconstructed CT slices as a post-processing operation. In other words, processing of the images is separated from the intraoperative or real-time diagnostic scanning procedure, although it can be done in the same computer/processor used in the imaging system 10 immediately after scanning or in a different computer/processor at a later time.

Figure 1:
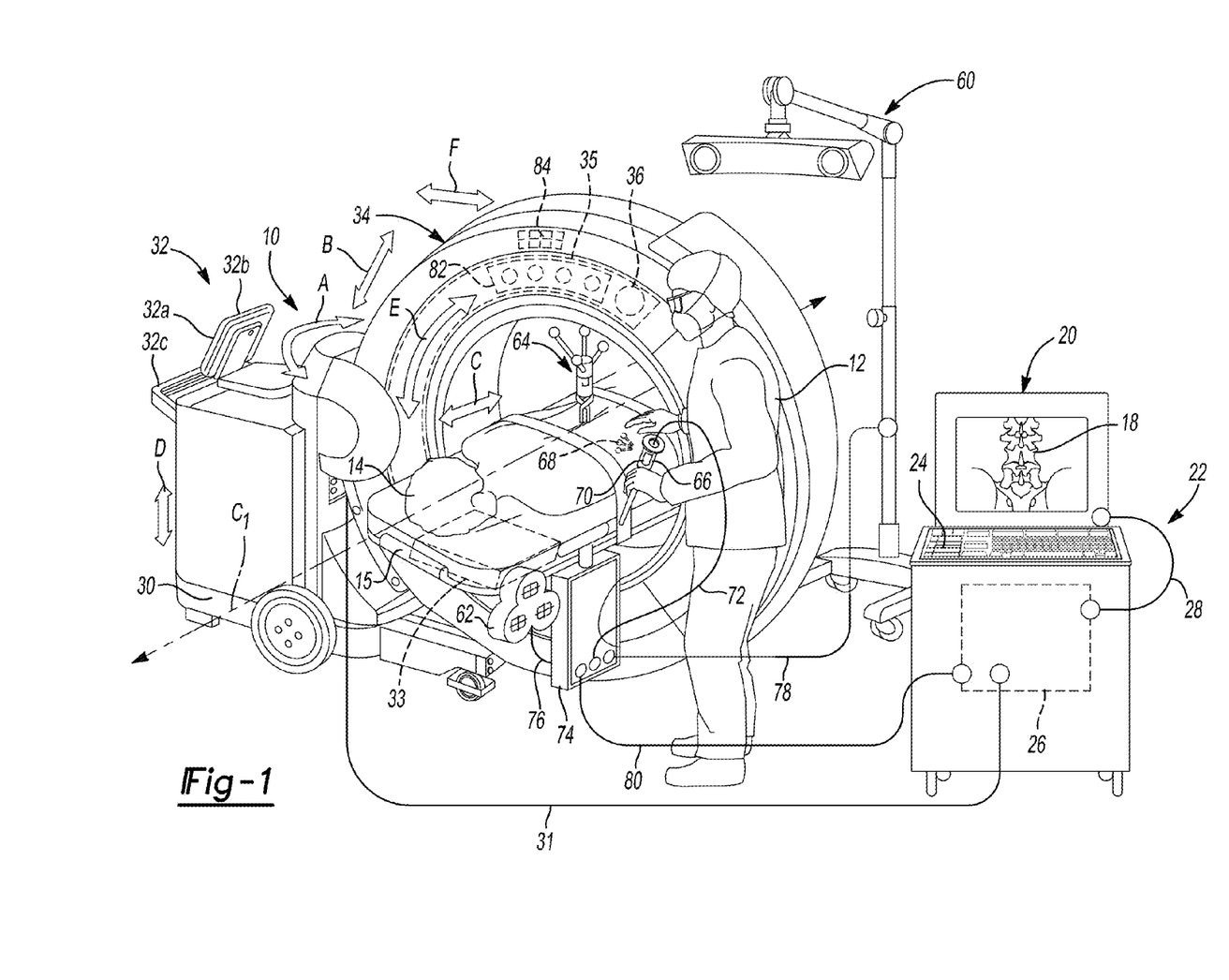
FIG. 1 is an environmental view of an exemplary imaging system.
Figure 2:
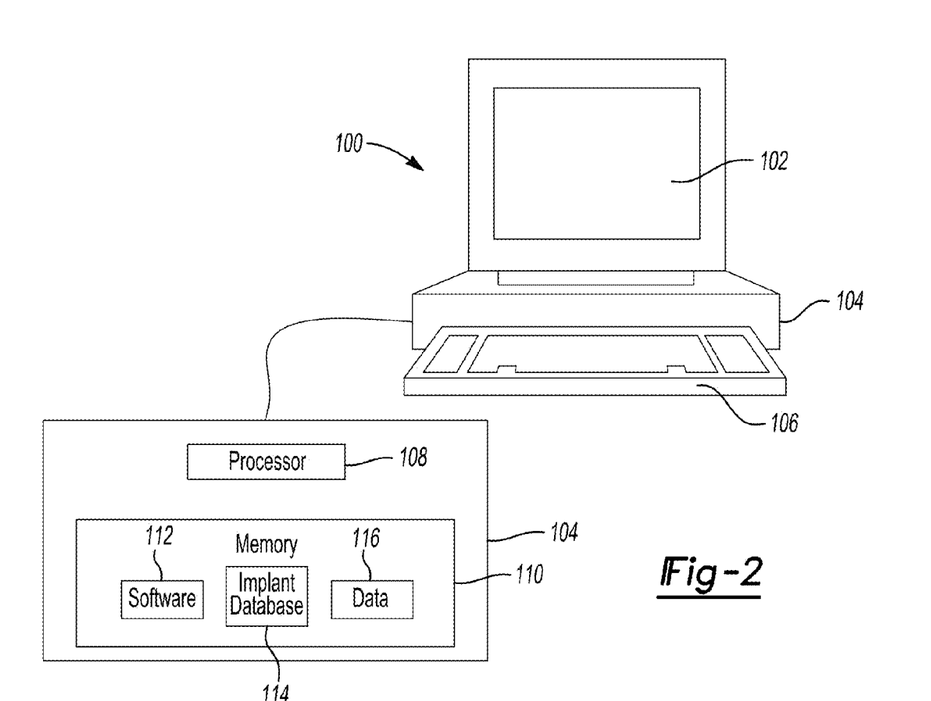
FIG. 2 is an exemplary computer system in use with the imaging system of FIG. 1.
Figure 3:
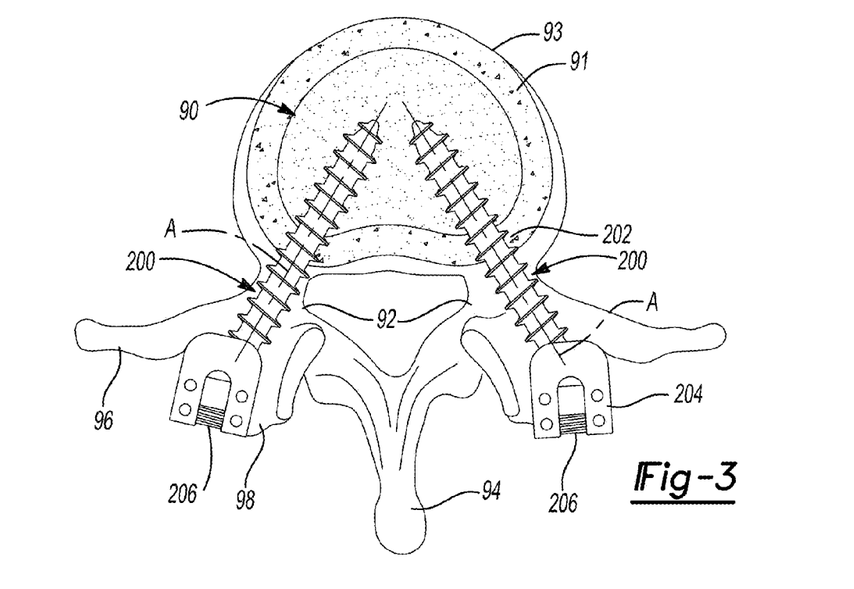
FIG. 3 is an environmental view of exemplary pedicle screws.
Figure 4:
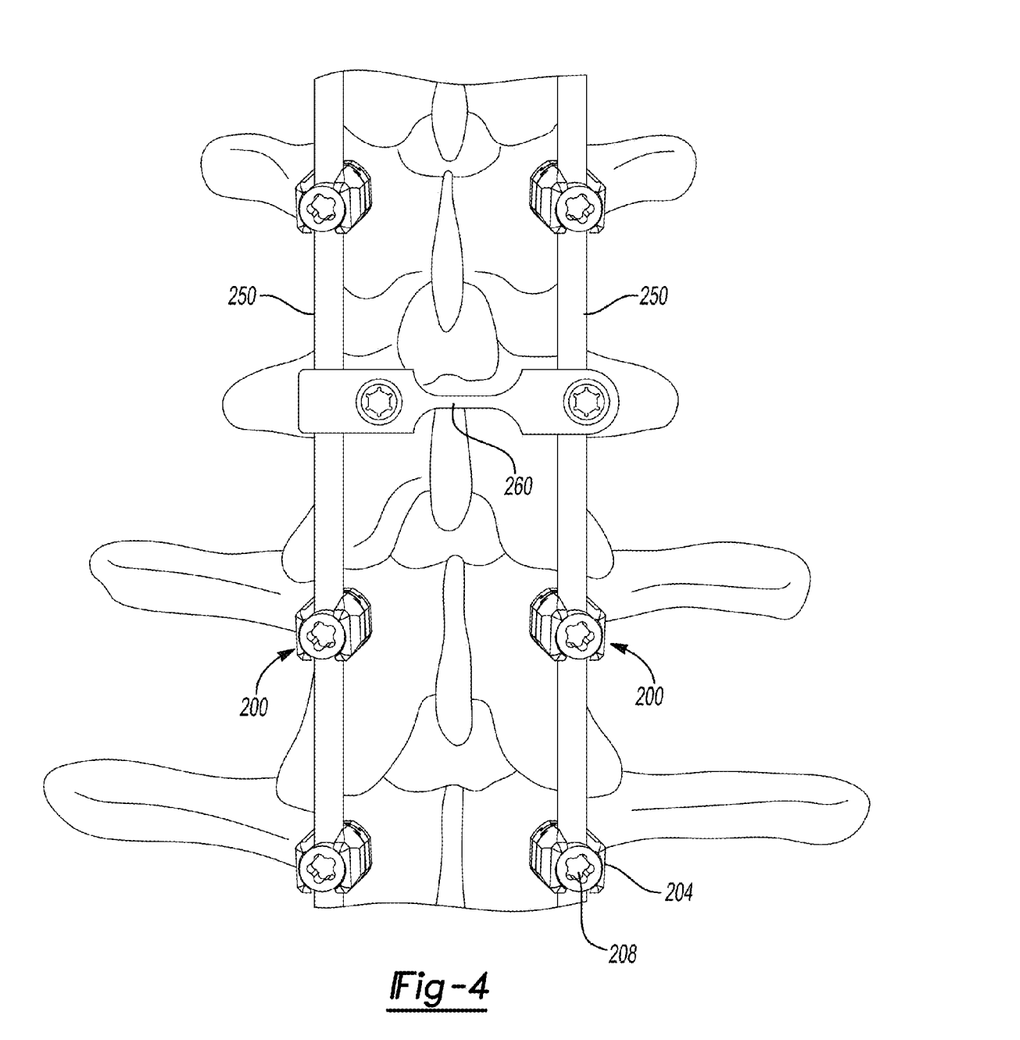
FIG. 4 is an environmental view of an exemplary spinal fixation implant including pedicle screws.
Figure 6:
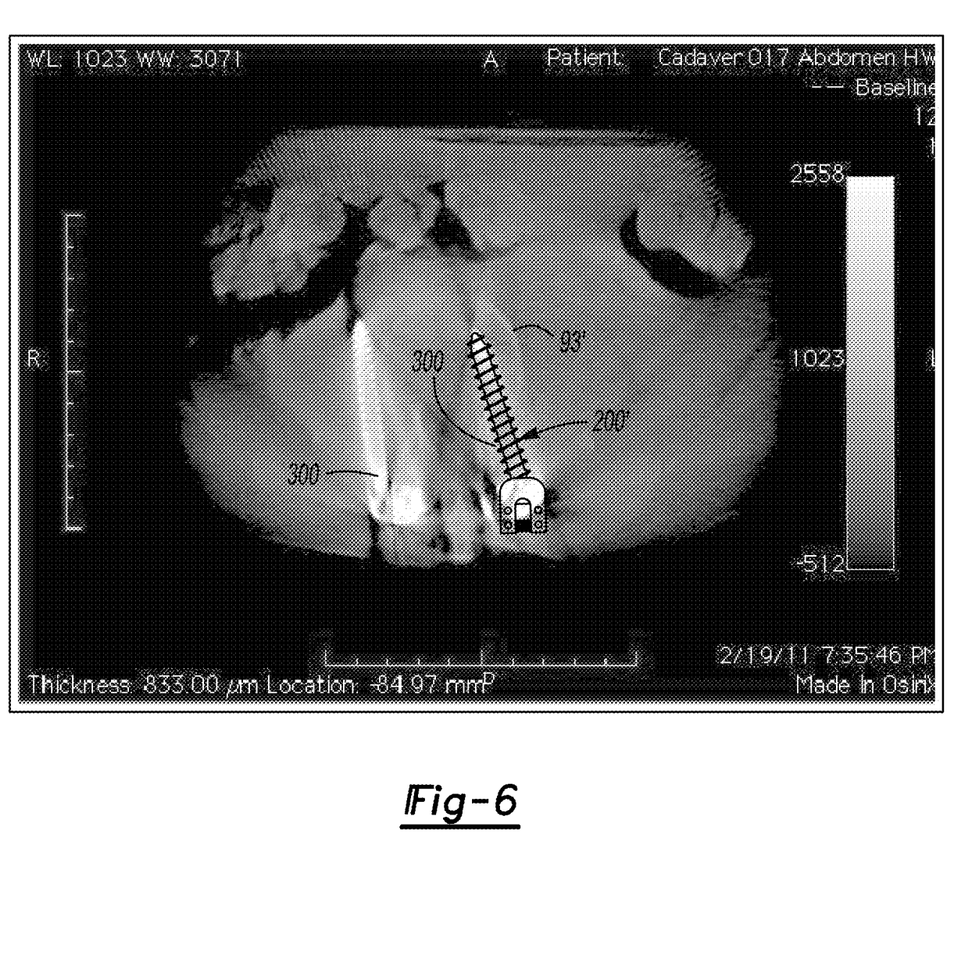
FIG. 6 is a scan image slice illustrating a correction of an artifact caused by an implant according to the present teachings.
Figure 7:
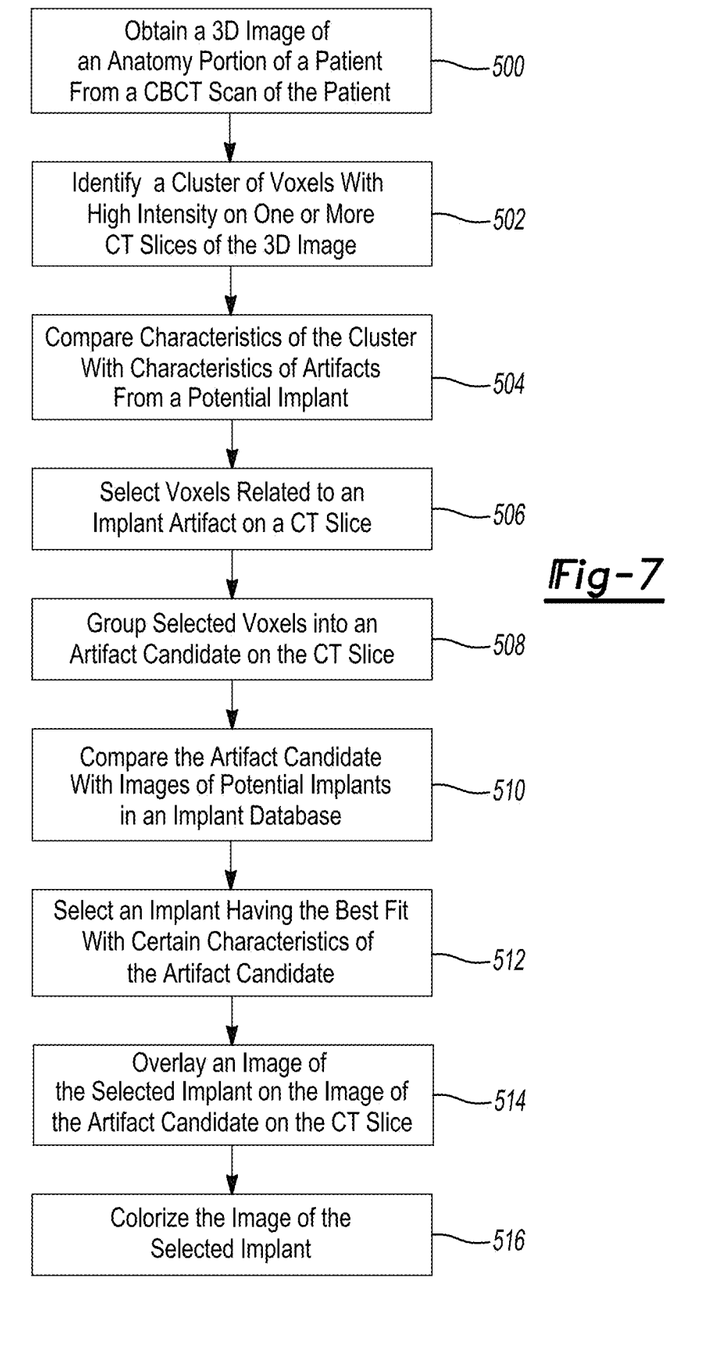
FIG. 7 is a flowchart of an exemplary method according to the present teachings.

Briefly, FIG. 1 illustrates various components of an exemplary CBCT imaging system 10 including x-ray source 36 and a flat panel detector 33. FIG. 2 illustrates a computer system for image processing that can be either part of the imaging system 10, or a separate system that can communicate with a computer or processing modules of the imaging system. FIGS. 3 and 4 illustrate exemplary metal implants associated with the spine. Although the method will be described using spine implants, such as pedicle screws, the present teaching are applicable and encompass to any implants capable of creating x-ray artifacts, including, for example, implants for hip, knee, shoulder, ankle, knee and other joints. The present teaching can also encompass other therapeutic implantable devices, such as cardiac pacing, defibrillation and resynchronization devices, or other implantable devices delivering therapy, including therapy by electrical signals or pulses. FIGS. 5A through 5F illustrate exemplary CT slices showing artifact associated with pedicle screws. FIG. 6 illustrates a CT slice with an image of identified implant overlaid on the artifact image. FIG. 7 is an exemplary flowchart of a method according to the present teachings.

With reference to FIG. 1, a user 12, such as a medical professional, clinician or other assistant, can perform a procedure on a subject, such as a human patient 14. In performing the procedure, the user 12 can use an imaging system 10 to acquire image data of the patient 14 for performing a procedure. The image data acquired of the patient 14 can include two-dimensional (2D) projections acquired with an x-ray imaging system, including those disclosed herein. It will be understood, however, that 2D forward projections of a volumetric model can also be generated, also as disclosed herein.

In one example, a model can be generated using the acquired image data. The model can be a three-dimensional (3D) volumetric model generated based on the acquired image data using various techniques, including algebraic iterative techniques and generate image data displayable on a display, referenced as displayed image data 18. Displayed image data 18 can be displayed on a display device 20, and additionally, can be displayed on a display device 32a associated with an imaging computing system 32. The displayed image data 18 can be a 2D image, a 3D image, or a time changing four-dimensional image. The displayed image data 18 can also include the acquired image data, the generated image data, both, or a merging of both types of image data.

It will be understood that the image data acquired of the patient 14 can be acquired as 2D projections, for example with an x-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22, which can be the same as the image processing computing system 100 shown in FIG. 2 . . . =The computing system 22 can include a variety of computer-readable media. The computer-readable media can be any available media that can be accessed by the computing system 22 and can include both volatile and non-volatile media, and removable and non-removable media. The computer-readable media can include, for example, computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can include any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, the computing system 22 could be integrated within or be part of the imaging computing system 32 associated with the imaging system 10 or the image processing computing system 100 shown in FIG. 2. A wired or wireless connection 28 can be provided between the computing system 22 and the display device 20 for data communication to allow driving the display device 20 to illustrate the image data 18.

The imaging system 10, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, U.S. Publication No. 2010-0290690, incorporated herein by reference. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference.

Referring to FIG. 1, the imaging system 10 can include a mobile cart 30 that includes the imaging computing system 32 and an imaging gantry 34 with a source 36, a collimator 37, a flat panel detector 33 (or other type of detector) and a rotor 35. With reference to FIG. 1, the mobile cart 30 can be moved from one operating theater or room to another and the gantry 34 can move relative to the mobile cart 30, as discussed further herein. This allows the imaging system 10 to be mobile so that it can be used in multiple locations and with multiple procedures without requiring a capital expenditure or space dedicated to a fixed imaging system.

With continued reference to FIG. 1, the gantry 34 can define an isocenter of the imaging system 10. In this regard, a centerline C1 through the gantry 34 can define an isocenter or center of the imaging system 10. Generally, the patient 14 can be positioned along the centerline C1 of the gantry 34, so that a longitudinal axis of the patient 14 can be aligned with the isocenter of the imaging system 10.

With reference to FIG. 2, a diagram is provided that illustrates an exemplary embodiment of an image processing computing system 100 which can include the imaging computing system 32 or computing system 22, or can be a separate computing system. The imaging computing system 100 can include a variety of computer-readable media. The computer-readable media can be any available media that can be accessed by the imaging computing system 100 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

In one example, the image processing computing system 100 comprises a display device 102 and a system unit 104. As illustrated, the display device 104 can comprise a computer video screen or monitor. The image processing computing system 100 can also include at least one input device 106. The system unit 104 can include, as shown in an exploded view, a processor 108 and a memory 110, which can include software with an image processing module (software) 112, an implant database 114 and other data 116, as shown in FIG. 2.

In this example, the at least one input device 106 comprises a keyboard. It should be understood, however, that the at least one input device 106 can comprise any suitable device to enable a user to interface with the image processing computing system 100, such as a touchpad, touch pen, touch screen, keyboard, mouse, joystick, trackball, wireless mouse, audible control or a combination thereof. Furthermore, while the image processing computing system 100 is described and illustrated herein as comprising the system unit 104 with the display device 102, the image processing computing system 100 could comprise a touchpad or tablet computing device or use display device 20.

Briefly, with reference to FIG. 1, the source 36 can emit x-rays through the patient 14 to be detected by the flat panel detector 33. The x-rays can be emitted by the source 36 in a cone beam and can be further shaped by an optional collimator 37 for detection by the flat panel detector 33. An exemplary collimator 37 is commercially available as the Compact Square Field Collimator sold by Collimare Engineering of Wheat Ridge, Colo., USA and included with the O-Arm® imaging system sold by Medtronic Navigation, Inc. of Louisville, Colo., USA. Briefly, the collimator 37 can include one or more leaves, which can be controlled to shape the x-rays emitted by the source 36. As will be discussed, the collimator 37 can be used to shape the x-rays emitted by the source 36 into a beam that corresponds with the shape of the flat panel detector 33. The source 36, collimator 37 and the flat panel detector 33 can each be coupled to the rotor 35.

Generally, the flat panel detector 33 can be coupled to the rotor 35 so as to be diametrically opposed from the source 36 and the collimator 37 within the gantry 34. The flat panel detector 33 can move rotationally in a 360° motion around the patient 14 generally in the directions of arrow E, and the source 36 and collimator 37 can move in concert with flat panel detector 33 such that the source 36 and collimator 37 remain generally 180° apart from and opposed to the flat panel detector 33.

The gantry 34 can isometrically sway or swing (herein also referred to as iso-sway) generally in the direction of arrow A, relative to the patient 14, which can be placed on a patient support or table 15. The gantry 34 can also tilt relative to the patient 14, as illustrated by arrows B, move longitudinally along the line C relative to the patient 14 and the mobile cart 30, can move up and down generally along the line D relative to the mobile cart 30 and transversely to the patient 14, and move perpendicularly generally in the direction of arrow F relative to the patient 14 to allow for positioning of the source 36, collimator 37 and flat panel detector 33 relative to the patient 14.

The imaging system 10 can be precisely controlled by the image processing computing system 32 to move the source 36, collimator 37 and the flat panel detector 33 relative to the patient 14 to generate precise image data of the patient 14. In addition, the imaging system 10 can be connected with the processor 26 via connection 31 which can include a wired or wireless connection or physical media transfer from the imaging system 10 to the processor 26. Thus, image data collected with the imaging system 10 can also be transferred from the image processing computing system 32 (or 100) to the computing system 22 (or 100) for navigation, display, reconstruction, post-processing etc.

Briefly, with continued reference to FIG. 1, according to various embodiments, the imaging system 10 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 14. If desired, the components associated with performing a navigated procedure could be integrated within the imaging system 10. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 31, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 and without direct viewing of the instrument 66 within the patient 14. For example, the instrument 66 could be graphically illustrated as an icon superimposed on the image data 18.

Further, the imaging system 10 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, the flat panel detector 33, rotor 35, the gantry 34, or other appropriate part of the imaging system 10 to determine the location or position of the source 36, the flat panel detector 33, rotor 35 and/or gantry 34 relative to a selected reference frame. As illustrated, the tracking device 82, 84 can be positioned on the exterior of the housing of the gantry 34. Accordingly, the imaging system 10 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206, filed on May 13, 2009.

In one example, the image data 18 can comprise a single 2D image. In another example, an image control/processing module, such as image processing module 112 (FIG. 2) can perform automatic reconstruction of an initial three dimensional model of the area of interest of the patient 14. Reconstruction of the three dimensional model can be performed in any appropriate manner, such as using algebraic techniques for optimization. Appropriate algebraic techniques include Expectation maximization (EM), Ordered Subsets EM (OS-EM), Simultaneous Algebraic Reconstruction Technique (SART) and total variation minimization. Their application to performing a 3D volumetric reconstruction based on the 2D projections allows for efficient and complete volumetric reconstruction.

Generally, an algebraic technique can include an iterative process to perform a reconstruction of the patient 14 for display as the image data 18. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. In this regard, the stylized model can provide additional detail regarding the anatomy of the patient 14, which can enable the user to plan the surgical intervention much more efficiently. The theoretical model can be associated with theoretical image data to construct the theoretical model. In this way, the model or the image data 18 can be built based upon image data acquired of the patient 14 with the imaging system 10. The image processing module 112 can output image data 18 to the display device 32a or 102.

Referring to FIGS. 3 and 4, an exemplary implant 200 that may cause imaging artifacts in CT scans is illustrated in superior view of a lumbar vertebra 90 (such as L2 vertebra). The vertebra 90 includes a vertebral body 91, a spinous process 94, transverse processes 96, pedicles 92 between the body 91 and the transverse processes 96, and superior articular processes 98. The vertebra has a cortical bone contour 93 surrounding an internal trabecular (cancellous) bone. The cortical bone contour 93, because of it greater density, appears brighter than the spongy trabecular bone on the x-ray images. The implant 200 is a pedicle screw (two pedicle screws 200 are shown in FIG. 3). The pedicle screw 200 includes a head 206 and a threaded shaft 202 having a longitudinal axis A. The pedicle screws 200 are inserted through the pedicle such that their axes are directed toward the apex of the vertebral body 91. The head of the screw 206 is captured by a receiver or seat 204 that is also used for coupling to elongated rods 250 of a spinal fixation system shown in FIG. 4. As shown in FIG. 4, the elongated rods 250 can be secured in the receivers 204 with corresponding locking plugs 208. The heads 206 of the screws are at lower portions of the receivers 204 under the elongated rods 250.

Figure 5A:
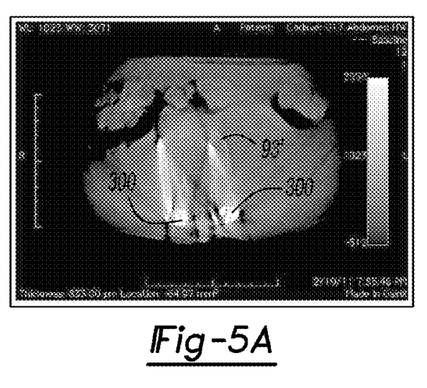
FIG. 5A is a first scan image slice illustrating an artifact caused by an implant.
Figure 5B:
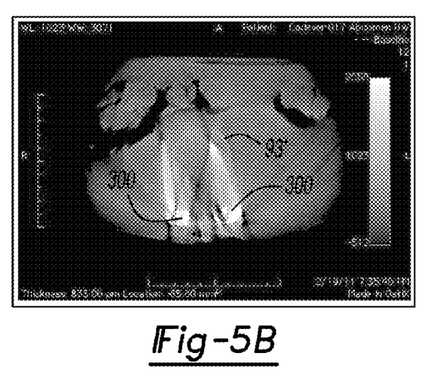
FIG. 5B is a second scan image slice illustrating an artifact caused by the implant of FIG. 5A.
Figure 5C:
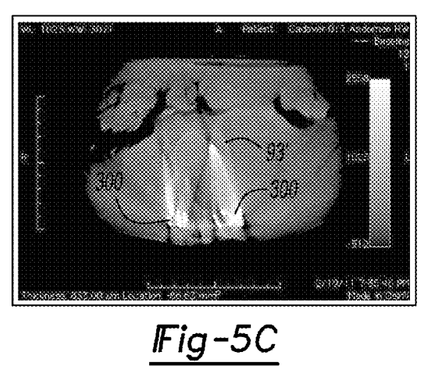
FIG. 5C is a second scan image slice illustrating an artifact caused by the implant of FIG. 5A.
Figure 5D:
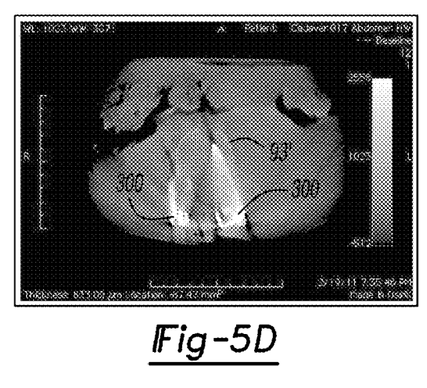
FIG. 5D is a second scan image slice illustrating an artifact caused by the implant of FIG. 5A.
Figure 5E:
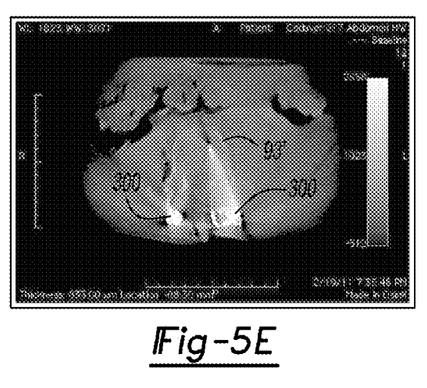
FIG. 5E is a second scan image slice illustrating an artifact caused by the implant of FIG. 5A.
Figure 5F:
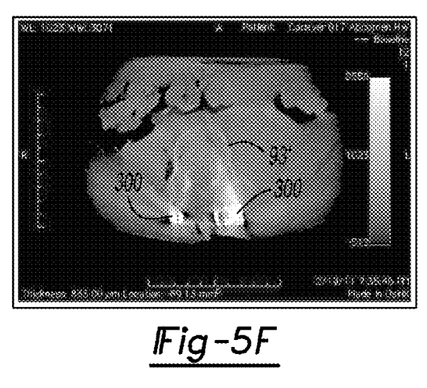
FIG. 5F is a second scan image slice illustrating an artifact caused by the implant of FIG. 5A.

Referring to FIGS. 5A through 5F, images from six CT slices of thickness 833.00 µm at six corresponding locations −84.97 mm, 0.85.40 mm, −86.63 mm, −87.47 mm, −88.30 mm and −89.13 relative to a tagged or reference image (not shown) are illustrated. The images are of a posterior cadaveric spine having two implanted pedicle screws, such as those discussed in connection to FIGS. 3 and 4. In the following description, reference numerals from FIG. 3 are used to describe corresponding elements of the vertebra and pedicle screws in the images of the CT of FIGS. 5A through 5F. In each CT slice, the left and right side of the patient is identified by the letters L and R. To avoid confusion, the left and right sides L and R will be references as radiological left and right (opposite of the left and right sides of the figures). The artifacts 300 around the pedicle screws 200, i.e., areas of increased brightness and "blooming" effects, vary depending of on the location of the CT slices. In some of the CT slices, the image of cortical contour 93' of the vertebral body (shown at 93 in FIG. 3) is obscured, hindering an assessment of whether the pedicle screws 200 are correctly implanted such that their longitudinal axes A are directed toward the apex of the vertebral body 91. For example, the CT slices of FIGS. 5B, 5C, 5D and 5E have the worse artifacts 300 in the sense that the blooming effects become broader and obscure the image of cortical contour 93', making it difficult to determine whether the pedicle screws 200 are correctly positioned. In FIG. 5A, although there is still a lot of artifact 300, the outline or edges of the pedicle screws 200 are visible. In FIG. 5B, the blooming effect is broader, obscuring the cortical contour 93' and making the determination of the direction and location of the left pedicle screw 200 (radiological left marked by L; appears on the right side of FIG. 5B). The blooming effect becomes worse in FIGS. 5C and 5D, and then gradually improves from FIG. 5E to FIG. 5F. Assessing FIGS. 5A and 5F, for example, we can determine that (radiological) right pedicle screw has deviated significantly medially away from the right pedicle 92. Similarly, the (radiological) left pedicle screw 200 appears to be misoriented and very close to spinal canal.

The present teachings provide a method that can identify the particular implant that causes the artifact 300 and overlay a CAD, graphical or other scaled image 200' in outline over the artifact 300, thereby indicating its actual position and orientation, as shown, for example, in FIG. 6. In FIG. 6, the outline of a pedicle screw is overlaid on the radiological left blooming artifact 300, reliably indicating the actual position of the implanted left pedicle screw 200' as well as the shape, size and or type of implanted pedicle screw 200 on the CT slice displayed on a display of computing system, such as display 102 of FIG. 2. An embodiment of the method to position the overlay is briefly outlined in the flowchart of FIG. 7.

As described in reference with FIG. 1, the x-ray source 36 can direct a cone beam of x-rays toward the flat panel detector 36. The subject 14 is positioned such that the region of interest is within the cone beam. By rotating the x-ray source and the detector around the subject 14, a plurality of 2D projections of the region of interest is acquired at block 500 of FIG. 7. The projections can be processed by CBCT reconstruction software to obtain the 3D image of the corresponding anatomy of the subject 14. As discussed above the reconstruction software can be incorporated in the image computing system 32 or computing system 22 or in the image processing system 100, which may separate and communicating systems, overlapping systems or integrated in one system.

Either automatically or by user input, for example, through the input device 106 of FIG. 2, identification of voxels with higher intensity relative to the expected intensity thresholds for bones and tissue of the patient's anatomy is initiated in one or more selected CT slices of the 3D image. A post-processing software module configured to execute image processing commands is incorporated in the image processing module 112 and can identify and locate clusters of voxels that are brighter or have higher contrast than the average brightness of surrounding voxels in a CT slice for the particular range of intensity of the x-ray source 36, at block 502. Isolated voxels of higher than a given threshold intensity may be discarded and adjacent voxels higher than the given threshold intensity may be grouped together for further analysis and identification. To determine whether a cluster of voxels is an artifact of an implant (i.e., an implant candidate), such as a metallic or ceramic screw or other implant, various factors or characteristics of the cluster can be compared with corresponding characteristics of artifacts from a potential implant, at block 504. Characteristics that can be compared include intensity of the image, mass attenuation, density and material composition. These characteristics can be stored in the implant database 114 (FIG. 2), which can include the tables of such properties for common implants for a particular anatomy, such as spinal implants, hip and knee implants or orthopedic and non-orthopedic implants. For example, when a portion of the patient's lumbar spine is imaged, the characteristics of various fixation implants, such as pedicle screws, fixation rods and other implants can be included in the database. In the case of pedicle screws, for example, the database can include the composition, size, shape and orientation relative to vertebral bodies in exemplary spinal fixation or other spinal corrective procedures as well as expected artifact shapes, sizes, brightness, attenuation, density, etc., for comparison. Based on the comparison, voxels potentially related to an implant artifact are selected on a CT slice at block 506 and grouped into an implant candidate (or artifact candidate for an implant) at block 508. At block 510, the implant candidate, i.e., the selected cluster of voxels, can be selected using a best fit analysis and optionally statistical and reliability evaluations of the available data for various characteristics, such as those discussed above. The implant candidate is compared to images and artifacts of potential implants from the implant database 114 at block 510 and a best fit implant is selected from the implant database 114 at block 512. The best fit selection of the implant candidate and corresponding implant can be based on a least square, iterative, weighted or other optimization or probability algorithm. The best-fit algorithm can employ a weighted metric that includes image intensity, mass density, material composition and or other characteristics with corresponding weight factors. The weight factors can be optional or selected based on information available in a database of prior results or other knowledge and experience. The weight factors can be equal, unequal and include zero and nonzero combinations. For example, in some embodiment the image intensity and mass composition can be weighted equally at 50% each, while the mass density is weighted at 0%. In other embodiments, all factors can be weighted equally. The selection of the best fit implant includes, in addition to the inherent characteristics of the selected implant (such as shape, size, type, material composition, etc.), a determination of the orientation and location of the implant relative to the artifact and/or anatomic landmarks on the CT slice. A stylized, CAD, graphical or other image of the selected implant 200' can be overlaid and registered with the determined orientation and location on the CT slice at block 514, as also shown in FIG. 6. The image of the selected implant can be rendered in a selectable color and with a selectable degree of transparency at block 516.

Referring to FIG. 2, the method is performed in an automated manner by the image processing module 112 using the reconstructed 3D image as an input and providing one or more CT slices showing an image of the detected and identified implant overlaid on the CT slices. Optionally, interactive input from a user at an input device 106 can be enabled at the start of the method. Such input can be provided, for example, at blocks 502 to 516 to take advantage of the sometimes superior image recognition performance of the human eye, or verify a selection made by the image processing module 112. Additionally, input regarding the location of CT slices in the 3D image can be provided as an input by the user. An exemplary and simplified flowchart of an interactive processing session is illustrated in FIG. 8.

Figure 8:
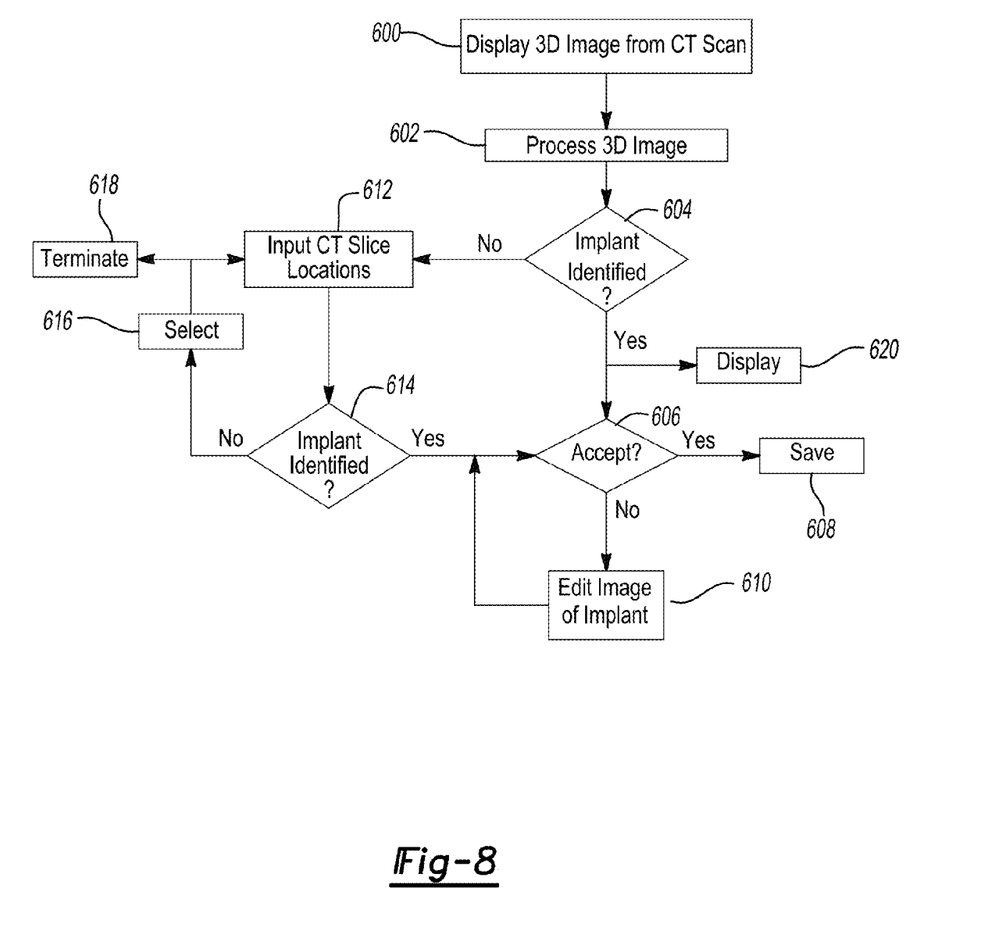
FIG. 8 is a flowchart of an exemplary interactive method according to the present teachings.

Referring to FIGS. 2 and 8, a 3D image reconstructed from the 2D projections taken with the imaging system 10 is displayed on the display 102 of the image processing computing system 100 at block 600 of FIG. 8. The 3D image can be processed according to the preset teachings, for example according to the method of FIG. 7, at block 602 to determine whether an implant has been identified at block 604. If an implant is identified, then the image of the implant overlaid on a CT slice, such as in FIG. 6, can be shown on the display at block 620. The user can be prompted to either accept or reject the overlaid implant image at block 606. If the user accepts the implant image, the implant image can be saved at block 608. If the user rejects the implant image, the user can edit the implant image at block 610. Editing of the implant image at block 610 can include adding or removing colorization of the implant, changing the transparency of the implant image, moving or rotating the image relative to the associated artifact, zooming, changing contrast and performing image editing actions using the input device 106.

With continued reference to FIG. 8, if no implant is identified at block 604, the user can be prompted to input different locations for CT slices, visually examine the new CT slices and/or direct the processor to repeat the identification and detection computational routine at block 612. If an implant is identified at block 614, then the user can be prompted to accept or reject the identified implant at 606 as described above. If no implant is identified, the user can be prompted at block 616 to ether terminate the routine at block 618 or return to block 612 and repeat the process.

The present teachings provide a computer-implemented method for identifying and displaying implants from artifacts in CT slices of a 3D image of a patient's anatomy. The 3D image can be reconstructed from 2D projections of a CT or CBCT imaging system, such as, for example, the imaging system 10, in a processor (such as processor 108 of FIG. 2) of a computing system associated with the imaging system, such as, for example, the computing system 32 or 22 shown in FIG. 1 or the computing system 100 shown in FIG. 2. While the 3D image reconstruction can be performed during the imaging session (intraoperatively), the identification of implants causing artifacts is a post-processing procedure performed using axial sections or CT slices. The processor 108 compares the intensity and contrast characteristics of voxels in the 3D image and various CT slice locations and selects clusters of voxels with characteristics associated with known implant artifacts. The characteristics of each identified cluster of voxels are compared with similar characteristics of artifacts of known implants in an implant database, such as implant database 114 in FIG. 2. Least square or other optimization and reliability algorithms can be used to select the best fit implant for a selected artifact that is an implant candidate. An image of the identified implant can be registered and overlaid in the scale of the CT slice on the image of the CT slice in the display 102 of the image processing computing system 100. The image of the implant can be a wire or solid CAD drawing or other digital rendering of the implant and include colorization of a contour of the image or filler colorization of the image of the implant with selected degrees of transparency, contrast and shades of color to enhance recognition and identification of the image of the implant on the CT slice.

Summarizing, the present teachings provide a method of detecting an identifying an implant in a CT slice of a reconstructed 3D image of a patient's anatomy. The method analyzes and identifies voxels associated with image artifacts and compares clusters of selected voxels with artifact characteristics associated with implants in an implant database. A best fit implant is determined and an image of the best fit implant is registered and overlaid on the CT slice and viewed on a display of an image processing computing system. This information enables the user to better assess and evaluate the condition of recent or old therapy or procedure and plan a corrective or new procedure taking into account the location and orientation of the implant and its characteristics.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A system comprising:
a memory configured to store (i) a first predetermined characteristic of an artifact of a first implant, and (ii) a non-x-ray image of the first implant; and
a processor configured to
receive an x-ray image of a patient, wherein the x-ray image of the patient includes an x-ray image of an implant in the patient,
based on the x-ray image of the patient, identify a cluster of voxels, wherein the cluster of voxels is an artifact of the implant in the patient,
determine a first characteristic of the cluster of voxels,
compare the first characteristic of the cluster of voxels to the first predetermined characteristic to determine whether the implant in the patient is the first implant, and
overlay the non-x-ray image on the x-ray image based on a result of the comparison between the first characteristic of the cluster of voxels and the first predetermined characteristic.

2. The system of claim 1, wherein:
the memory is configured to store (i) a plurality of predetermined characteristics of artifacts of a plurality of implants, and (ii) non-x-ray images of the plurality of implants;
the plurality of implants include the first implant and a second implant;
the processor is configured to compare the characteristic of the cluster of voxels to the plurality of predetermined characteristics of the artifacts of the plurality of implants;

determining the first predetermined characteristic of the artifact of the first implant better matches the first characteristic of the cluster of voxels than the predetermined characteristic of the artifact of the second implant; and overlaying the non-x-ray image of the first implant on the x-ray image of the implant in the patient as a result of the first predetermined characteristic of the artifact of the first implant better matching the first characteristic of the cluster of voxels than the predetermined characteristic of the artifact of the second implant.

3. The system of claim 1, wherein the processor is configured to, in comparing the first characteristic of the cluster of voxels to the first predetermined characteristic:

compare an image intensity of the cluster of voxels to an intensity level corresponding to the artifact of the first implant; and overlay the non-x-ray image on the x-ray image based on a result of the comparison between the image intensity of the cluster of voxels and the intensity corresponding to the artifact of the first implant.

4. The system of claim 1, wherein the processor is configured to, in comparing the first characteristic of the cluster of voxels to the first predetermined characteristic:

compare a mass density of the implant in the patient to a mass density of the first implant; and overlay the non-x-ray image on the x-ray image based on a result of the comparison between the mass density of the implant in the patient and the mass density of the first implant.

5. The system of claim 1, wherein the processor is configured to, in comparing the first characteristic of the cluster of voxels to the first predetermined characteristic:

compare a material composition of the implant in the patient to a material composition of the first implant; and overlay the non-x-ray image on the x-ray image based on a result of the comparison between the material composition of the implant in the patient and the material composition of the first implant.

6. The system of claim 1, wherein:

the memory is configured to store (i) a second predetermined characteristic of an artifact of a second implant, and (ii) a non-x-ray image of the second implant; and the processor is configured to
receive a second x-ray image,
identify a second cluster of voxels, wherein the second cluster of voxels is a second artifact of the implant in the patient,
compare a second characteristic of the second cluster of voxels to the second predetermined characteristic of the artifact of the second implant, and
overlay the non-x-ray image of the second implant on the x-ray image of the implant in the patient based on the comparison between the second characteristic of the second cluster of voxels and the second predetermined characteristic of the artifact of the second implant.

7. The system of claim 1, wherein:

the processor is configured to, while identifying the cluster of voxels, compare an intensity level of each of the voxels with a threshold intensity level; and the threshold intensity level is based on coefficients of attenuation corresponding to tissues surrounding the implant in the patient.

8. The system of claim 1, the processor is configured to:

determine a weighted metric based on (i) an image intensity level of the cluster of voxels, (ii) a mass density of the implant in the patient, and (iii) a material composition of the implant in the patient, wherein the weighted metric includes a respective weight factor for each of the image intensity level, the mass density, and the material composition; and selecting the first implant from a plurality of implants based on the weighted metric.

9. The system of claim 1, wherein:

the memory is configured to store a plurality of predetermined characteristics of the artifact of the first implant;

the plurality of predetermined characteristics comprise the first predetermined characteristic; and the processor is configured to
determine a plurality of characteristics of the cluster of voxels, wherein the plurality of characteristics of the cluster of voxels includes the first characteristic of the cluster of voxels,
compare the plurality of characteristics of the cluster of voxels to the plurality of predetermined characteristics to determine whether the implant in the patient is the first implant, and
overlay the non-x-ray image on the x-ray image based on a result of the comparison between the plurality of characteristics of the cluster of voxels and the plurality of predetermined characteristics.

10. The system of claim 9, wherein the plurality of characteristics of the cluster of voxels comprise a brightness level, a contrast level, an intensity level, and an attenuation value.

11. The system of claim 9, wherein the plurality of characteristics of the artifact of the first implant comprise a composition, a size, a shape, and an orientation relative to a vertebral body.

12. The system of claim 9, wherein the plurality of characteristics of the artifact of the first implant comprise a shape, a size, a brightness level, and an attenuation value.

13. The system of claim 1, the processor is configured to:

receiving a user input;
reject the first implant based on the user input;
in response to rejecting the first implant, identify a second cluster of voxels of the implant in the patient;
compare a characteristic of the second cluster of voxels to a characteristic of an artifact of a second implant; and
overlay a non-x-ray image of the second implant on the x-ray image of the implant in the patient based on the comparing of the characteristic of the second cluster of voxels to the characteristic of the artifact of the second implant.

14. A method comprising:

storing in a memory (i) a first predetermined characteristic of an artifact of a first implant, and (ii) a non-x-ray image of the first implant;

receiving an x-ray image of a patient, wherein the x-ray image of the patient includes an x-ray image of an implant in the patient;

based on the x-ray image of the patient, identifying a cluster of voxels via a processor, wherein the cluster of voxels is an artifact of the implant in the patient;

determining a first characteristic of the cluster of voxels;

comparing the first characteristic of the cluster of voxels to the first predetermined characteristic to determine whether the implant in the patient is the first implant; and overlaying the non-x-ray image on the x-ray image based on a result of the comparison between the first characteristic of the cluster of voxels and the first predetermined characteristic.

15. The method of claim 14, further comprising:

storing in the memory (i) a plurality of predetermined characteristics of artifacts of a plurality of implants, and (ii) non-x-ray images of the plurality of implants, wherein the plurality of implants include the first implant and a second implant;

comparing the characteristic of the cluster of voxels to the plurality of predetermined characteristics of the artifacts of the plurality of implants;

determining the first predetermined characteristic of the artifact of the first implant better matches the first characteristic of the cluster of voxels than the predetermined characteristic of the artifact of the second implant; and overlaying the non-x-ray image of the first implant on the x-ray image of the implant in the patient as a result of the first predetermined characteristic of the artifact of the first implant better matching the first characteristic of the cluster of voxels than the predetermined characteristic of the artifact of the second implant.

16. The method of claim 14, wherein the comparing of the first characteristic of the cluster of voxels to the first predetermined characteristic comprises:

comparing an image intensity level of the cluster of voxels to an intensity level corresponding to the artifact of the first implant; and overlaying the non-x-ray image on the x-ray image based on a result of the comparison between the image intensity of the cluster of voxels and the intensity corresponding to the artifact of the first implant.

17. The method of claim 14, wherein the comparing of the first characteristic of the cluster of voxels to the first predetermined characteristic comprises:

comparing a mass density of the implant in the patient to a mass density of the first implant; and overlaying the non-x-ray image on the x-ray image based on a result of the comparison between the mass density of the implant in the patient and the mass density of the first implant.

18. The method of claim 14, wherein the comparing of the first characteristic of the cluster of voxels to the first predetermined characteristic comprises:

comparing a material composition of the implant in the patient to a material composition of the first implant; and overlaying the non-x-ray image on the x-ray image based on a result of the comparison between the material composition of the implant in the patient and the material composition of the first implant.

19. The method of claim 14, further comprising:

storing in the memory (i) a second predetermined characteristic of an artifact of a second implant, and (ii) a non-x-ray image of the second implant;

receiving a second x-ray image;

identifying a second cluster of voxels, wherein the second cluster of voxels is a second artifact of the implant in the patient;

comparing a second characteristic of the second cluster of voxels to the second predetermined characteristic of the artifact of the second implant; and overlaying the non-x-ray image of the second implant on the x-ray image of the implant in the patient based on the comparison between the second characteristic of the second cluster of voxels and the second predetermined characteristic of the artifact of the second implant.

20. The method of claim 14, wherein:

identifying of the cluster of voxels comprises comparing an intensity level of each of the voxels with a threshold intensity level; and the threshold intensity level is based on coefficients of attenuation corresponding to tissues surrounding the implant in the patient.

21. The method of claim 14, further comprising:

determining a weighted metric based on (i) an image intensity level of the cluster of voxels, (ii) a mass density of the implant in the patient, and (iii) a material composition of the implant in the patient, wherein the weighted metric includes a respective weight factor for each of the image intensity level, the mass density, and the material composition; and selecting the first implant from a plurality of implants based on the weighted metric.

22. The method of claim 14, further comprising:

storing in the memory a plurality of predetermined characteristics of the artifact of the first implant, wherein the plurality of predetermined characteristics comprise the first predetermined characteristic;

determining a plurality of characteristics of the cluster of voxels, wherein the plurality of characteristics of the cluster of voxels includes the first characteristic of the cluster of voxels;

comparing the plurality of characteristics of the cluster of voxels to the plurality of predetermined characteristics to determine whether the implant in the patient is the first implant; and overlaying the non-x-ray image on the x-ray image based on a result of the comparison between the plurality of characteristics of the cluster of voxels and the plurality of predetermined characteristics.

23. The method of claim 22, wherein the plurality of characteristics of the cluster of voxels comprise a brightness level, a contrast level, an intensity level, and an attenuation value.

24. The method of claim 22, wherein the plurality of characteristics of the artifact of the first implant comprise a composition, a size, a shape, and an orientation relative to a vertebral body.

25. The method of claim 22, wherein the plurality of characteristics of the artifact of the first implant comprise a shape, a size, a brightness level, and an attenuation value.

26. The method of claim 14, further comprising:

receiving a user input;

rejecting the first implant based on the user input;

in response to rejecting the first implant, identifying a second cluster of voxels of the implant in the patient;

comparing a characteristic of the second cluster of voxels to a characteristic of an artifact of a second implant; and overlaying a non-x-ray image of the second implant on the x-ray image of the implant in the patient based on the comparing of the characteristic of the second cluster of voxels to the characteristic of the artifact of the second implant.

* * * * *